United States Patent [19]
Knoll et al.

[11] Patent Number: 5,116,121
[45] Date of Patent: May 26, 1992

[54] EXAMINATION OF PHYSICAL PROPERTIES OF THIN FILMS

[75] Inventors: Wolfgang Knoll, Mainz; Harald Knobloch, Albig, both of Fed. Rep. of Germany

[73] Assignee: BASF Aktiengesellschaft, Ludwigshafen, Fed. Rep. of Germany

[21] Appl. No.: 646,082

[22] Filed: Jan. 28, 1991

[30] Foreign Application Priority Data

Feb. 10, 1990 [DE] Fed. Rep. of Germany ....... 4004088

[51] Int. Cl.⁵ .......................... G01J 3/44; G01N 21/65
[52] U.S. Cl. ..................................................... 356/301
[58] Field of Search .......................................... 356/301

[56] References Cited
FOREIGN PATENT DOCUMENTS

EP-A-0403769 12/1990 European Pat. Off.
DE-C 3720387 11/1988 Fed. Rep. of Germany.

OTHER PUBLICATIONS

Surface Plasma Oscillations and Their Oscillations . . . Raether Physics of Thin Films, vol. 9, 145-361, New York 1977.
Surface Plasmon-Enhanced Raman Scattering at . . . Corn et al. J. Chem. Phys 80, May 15, 1984.
On the Laser-Wavelength Dependence of Plasmon Surface . . . Knobloch et al., J. Chem. Phys 91 Oct. 1, 1989.
Surface Plasmon Enhanced Raman Spectra of Monolayer . . . Knoll et al., J. Chem. Phys 77 Sep. 1, 1982.
Physical Methods of Chemistry, Kuhn et al., Spectroscopy of Monolayer Assemblies (Wiley, N.Y. 1972) part III B, chapter VII.
Multichannel Raman Spectroscopy with a Cooled CCD Iaging Detector Batchelder, ESN European Spectroscopy News, 80 (1988) 28-33.

*Primary Examiner*—F. L. Evans
*Attorney, Agent, or Firm*—Keil & Weinkauf

[57] ABSTRACT

The physical properties of thin films can be examined with polarized light using a method which comprises directing polarized light at a layer system, exciting plasmon surface polaritons therein and thereby creating Raman-scattered light within the layer or layer system under examination, and imaging said light on a detector using an imaging system.

15 Claims, 3 Drawing Sheets

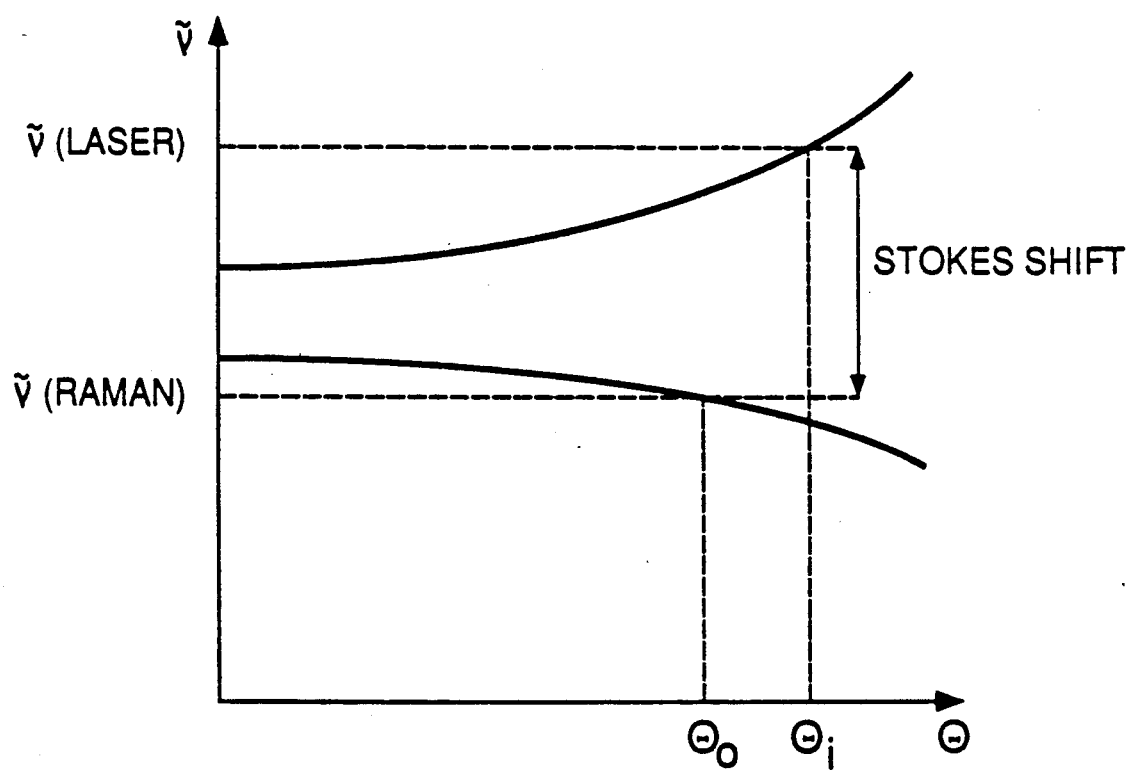

EXAMINATION OF PHYSICAL PROPERTIES OF THIN FILMS

The present invention relates to a method for examining physical properties of thin films with the aid of polarized light by using polarized light to excite plasmon surface polaritons in a layer system. The method according to the present invention makes it possible to carry out Raman-spectroscopic examinations with minimal hardware.

Plasmon surface polaritons (PSPs) are bound, non-radiative, electromagnetic modes which propagate along a metal/dielectric interface. Their field strength is at a maximum at the metal surface and decays exponentially not only into the metal but also into the dielectric (cf. H. Raether, in Physics of Thin Films Vol. 9, 145-261, New York 1977).

The interest in plasmon surface polaritons has increased in recent years, since they can be successfully used for field enhancement in the various surface-spectroscopic examinations of adsorbates and ultrathin films/layer systems (cf. R. M. Corn, M. R. Philpott, J. Chem. Phys. 80 (1984), 5245-49).

Raman scattering is a light scattering method in which the spectral position and intensity of the non-resonantly scattered light (here PSP) provide's information about the molecular structure of the examined sample (cf. Knobloch, Duschl, Knoll, J. Chem. Phys. 91 (1989), 3810-14); Raman-scattered light is shifted in the spectrum compared with the incident light (Stokes shift).

It is an object of the present invention to provide a method which makes it possible to carry out Raman-spectroscopic examinations of ultrathin films/layer systems with a minimum of optical components.

Whereas the existing methods for Raman-spectroscopic examinations require specific equipment for spectral analysis, for example monochromators, the method according to the present invention makes it possible to dispense with a monochromator or similar equipment for spectral analysis.

The method according to the present invention makes it possible to image the Raman-scattered light from the layer/layer system under examination directly on a camera with a lens. This is accomplished using surface-enhanced Raman spectroscopy by utilizing the angle dispersion and polarizing properties of plasmon surface polaritons (cf. Knoll et al., J. Chem. Phys. 77 (1982), 2254).

We have found, surprisingly, that the stated object is achieved by a method for the Raman-spectroscopic examination of ultrathin layers/layer systems (thickness $< 0.1$ $\mu$m) wherein the layers under examination have been applied to a solid support and are examined by means of surface-enhanced Raman spectroscopy as a function of the angle of incidence and the angle of observation.

The present invention accordingly provides a method for examining the physical properties of thin films with the aid of polarized light, which comprises directing polarized light at a layer system, exciting plasmon surface polaritons therein and thereat creating within Raman-scattered light the layer or layer system under examination, and imaging said light on a detector using an imaging system.

The plasmon surface polaritons are in general excited at a metal/ or semiconductor/dielectric interface.

To excite plasmon surface polaritons, the coupler used is in particular a prism or a grid structure on a solid surface.

In preferred embodiments of the method according to the present invention, a metal or semiconductor layer or the layer or layer system under examination is mounted on the coupler, or a metal or semiconductor layer and the layer under examination have been mounted on a solid support and this solid support has been disposed at a distance of 100-400 nm from the base of a prism.

The imaging system used is preferably a collecting lens, a lens system or a microscope objective.

It is advantageous to use a two-dimensional detector, in particular a low-noise camera, especially a CCD camera whose CCD chip is cooled with liquid nitrogen.

The present invention also provides a method for imaging the structured layer system under examination in the Raman-shifted region of the spectrum by imaging the structure of the layer under examination by utilizing the angle dispersion of plasmon surface polaritons as contrast mechanism, and also for the use of the method according to the present invention for Raman spectroscopy, wherein the angle dispersion of plasmon surface polaritons excited in the layer system under examination is utilized for the spectral resolution of the Raman lines.

The method according to the present invention is thus suitable not only for Raman-spectroscopic examination but also for imaging low-contrast but Raman-active samples of any kinds of thin organic films, for example lipid monolayers, cadmium arachidate, polyglutamates and polysilanes.

Plasmon surface polaritons are in general excited with a coupler in an Otto, Kretschmann or grid configuration using monochromatic, parallel, polarized light. The light source used is preferably an argon ion laser.

In the grid configuration, the layer/layer system under examination is applied to a metal or semiconductor layer whose surface has a grid structure. The grid structure is applied to the surface of the underlying glass substrate, preferably by means of holographic or lithographic techniques.

The coupling conditions for the exciting light beam and also for the Stokes-shifted Raman-scattered light are determined by the angle dispersion properties of the PSPs.

The spectral analysis of the Raman-scattered light is effected using the angle dispersion properties of the PSPs.

The thickness of the layer or layer systems under examination is in general $< 0.1$ $\mu$m, preferably $< 50$ nm, for example within the range from 5 to 40 nm.

Using the method according to the present invention it is possible to examine the following properties of thin, in particular ultrathin, films: optical layer thickness ($n \times d$), refractive index ($n$) and, particularly advantageously, the molecular polarizabilities of the layer under examination (for example monomolecular films and multilayer assemblies).

The layer or layer system under examination can be applied to metal or semiconductor layers in a conventional manner, for example by the Langmuir-Blodgett technique, by spin coating from solution, by vapor deposition and/or by adsorption from the gas or liquid phase, suitable metal layers being in general for example gold and in particular silver layers.

The Langmuir-Blodgett technique for fabricating thin films and multilayer assemblies is described for example in the paper by H. Kuhn, D. Möbius and H. Bücher in Physical Methods of Chemistry, edrs. A. Weissberger and B. W. Rossitter (Wiley, N.Y. 1972), part III B, chapter VII.

To this end, the solution of the substance to be examined, for example a lipid, in a low-boiling organic solvent, for example chloroform, is spread out at the water/air interface and, after the solvent has evaporated, is transferred in a conventional manner by the Langmuir-Blodgett technique to a metallic layer of a solid base material, for example a microscope slide made of glass which has been coated with silver and has been appropriately structured, for example with a holographic grid of a certain periodicity and modulation.

In addition, a system of optical filters can be used for spectral analysis and/or for suppressing scattered light.

BRIEF DESCRIPTION OF THE DRAWINGS

FIG. 3 is a graph of the dispersion of plasmon surface polaritons in grid coupling.

Figure 1:
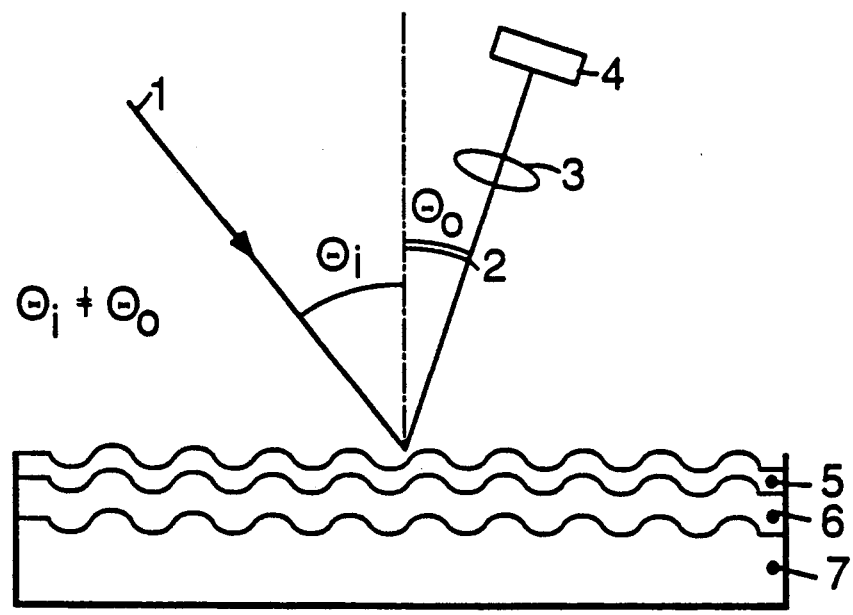
FIG. 1 illustrates an apparatus for use in the claimed method.

The construction of the apparatus used according to the present invention is depicted in diagrammatic form in FIG. 1, where 1 denotes the incident laser beam, 2 the Raman-scattered light, 3 the lens (a microscope objective), 4 the detector (CCD camera), 5 the layer under examination, 6 the metal layer, and 7 the microscope slide with a grid structure.

The sample prepared by the abovementioned methods is examined by means of PSP-enhanced Raman spectroscopy, meaning that the PSPs become coupled to the incident light via the grid/prism and are Raman-scattered. This Raman-scattered light is imaged by means of a lens onto a CCD camera, preferably cooled with liquid nitrogen, and recorded and can be stored for example on magnetic data media.

Suitable CCD cameras are described for example in D. N. Batchelder, ESN European Spectroscopy News, 80 (1988), 28-33. The method according to the present invention makes it possible to image the Raman-scattered light from the layer under examination directly on a camera.

EXAMPLE 1

8 layers of cadmium arachidate (CdA) are applied by the Langmuir-Blodgett technique to a microscope slide whose surface, which bears a holographic grid (periodicity: 0.5 μm, modulation 5 nm), has been vapor-deposited with a 100 nm thick coating of silver.

Using a UV lamp and a mask, a 1 mm wide stripe is desorbed off the sample (irradiation time: 30 minutes).

The light from the argon ion laser ($\lambda = 476.5$ nm) couples to the polaritons at an angle of incidence of 20°. The Raman-scattered light is collected by means of a lens at an angle of observation of 2° and is imaged through a monochromator on a nitrogen-cooled CCD camera. The image recorded with the CCD camera permits clear distinction between coated and desorbed areas.

If the incident light beam does not satisfy the PSP coupling conditions, it is impossible to discern any image, let alone any surface structure.

If the experimental setup is as above and the sample is prepared as above except that the CdA is half deuterated and half protonated, the image obtained on the CCD camera permits a clear distinction between protonated and deuterated areas.

It is thus possible to produce a contrast between the materials, despite the fact that the optical properties of the two materials are the same.

EXAMPLE 2

16 layers of cadmium arachidate (CdA) are applied by the Langmuir-Blodgett technique to a microscope slide whose surface, which bears a holographic grid (periodicity: 0.5 μm, modulation: 5 nm), has been vapor-deposited with a 100 mm thick coating of silver. The layer system thus prepared is structured through a mask by means of UV desorbtion (mercury vapor lamp exposure for 1 hour).

The light from the argon ion laser ($\lambda = 476.5$ nm) couples with the polariton field at an angle of incidence of 24°. The Raman-scattered light is imaged at an angle of observation of 6° by means of a lens system and a system of filters (long pass: Schott OG 15; interference filter: Pörschke TCV-072) on a nitrogen-cooled CCD camera.

The image recorded with the CCD camera clearly reveals coated and desorbed areas.

If the incident light beam does not satisfy the PSP coupling conditions, it is impossible to discern any image, let alone any surface structure.

A laser beam is incident upon the sample layer system under examination at a PSP resonance angle $\theta_i$, so that PSPs and the incident light are optimally coupled. The surface structure of the sample is imaged at an angle of observation $\theta_o$, through a lens and filter system, directly on a CCD camera.

Figure 2:
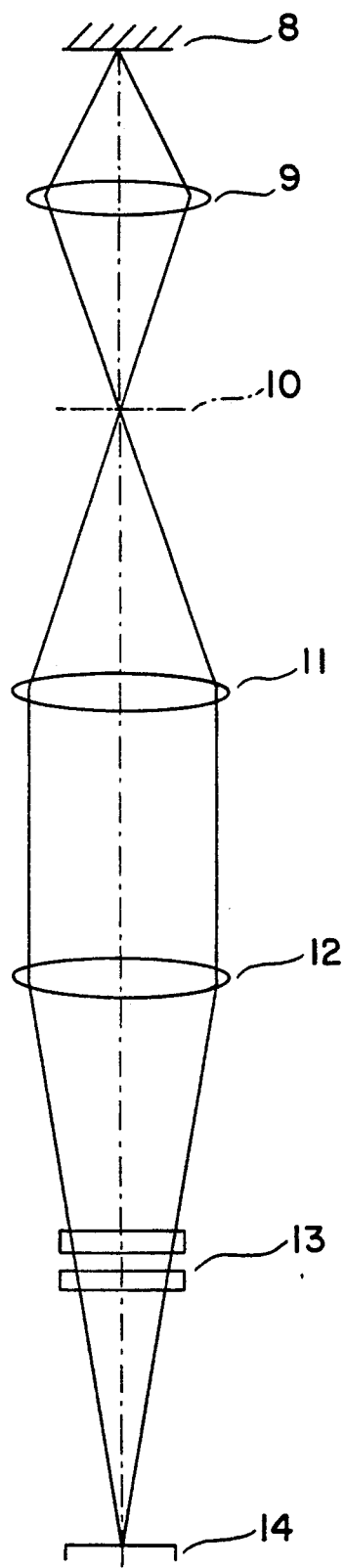
FIG. 2 illustrates a suitable lens and filter system for the apparatus for FIG. 1.

A suitable setup is shown in FIG. 2, where 8 denotes the sample (a layer system), 9, 11 and 12 each denote lenses, 10 denotes a diaphragm, 13 denotes a filter (filter system), and 14 denotes the CCD camera.

FIG. 3 shows the dispersion of plasmon surface polaritons in grid coupling, where $\bar{\nu}$ (laser) denotes the wavenumber of the incident laser light, $\bar{\nu}$ (Raman) denotes the wavenumber of the Raman-scattered light, $\theta_i$ denotes the PSP resonance angle for incident laser light, and $\theta_o$ denotes the angle of observation or the PSP resonance angle for Raman-scattered light.

We claim:

1. A method for examining the physical properties of a thin film layer with the aid of polarized light, which comprises directing polarized light at a layer system containing said layer, exciting plasmon surface polaritons therein and thereby creating Raman-scattered light within the layer or layer system under examination, and directly imaging said light on a detector using an imaging system.

2. The method of claim 1, wherein plasmon surface polaritons are excited at a metal/or semi-conductor/-dielectric interface.

3. The method of claim 2, wherein plasmon surface polaritons are excited using a coupler.

4. The method of claim 3, wherein the used is a prism.

5. The method of claim 3, wherein the coupler used is a grid structure on a solid surface.

6. The method of claim 3, wherein a metal or semiconductor layer or the layer or layer system under examination is mounted on the coupler.

7. The method of claim 3, wherein a metal or semiconductor layer and the layer under examination have been mounted on a solid support and this solid support has been disposed at a distance of from 100 to 400 nm, from the base of a prism.

8. The method of claim 4, wherein a metal or semiconductor layer and the layer under examination have been mounted on a solid support and this solid support has been disposed at a distance of from 100 to 400 mm from the base of a prism.

9. The method of claim 1, wherein in addition a system of optical filters is used to suppress scattered light other than Raman-scattered light.

10. The method of claim 1, wherein the imaging system used is selected from the group consisting of a collecting lens, a lens system and a microscope objective.

11. A method as claimed in claim 1, wherein the detector is two-dimensional.

12. The method of claim 11, wherein the detector is a low-noise camera.

13. The method of claim 12, wherein the camera is a CCD camera whose CCD chip is cooled with liquid nitrogen.

14. The method of claim 1, wherein the structure of the layer system under examination in the Raman-shifted region of the spectrum is imaged using the angle dispersion of plasmon surface polaritons as a contrast mechanism.

15. A method as claimed in claim 1 for use in Raman spectroscopy, wherein the angle dispersion of plasmon surface polaritons excited in the layer system under examination is utilized for the spectral resolution of the Raman lines.

* * * * *